(12) United States Patent
Su et al.

(10) Patent No.: US 7,749,764 B2
(45) Date of Patent: Jul. 6, 2010

(54) ELECTROCHEMICAL METHOD FOR DETECTING HEMOGLOBIN

(75) Inventors: Chein-Shyong Su, Taipei (TW); Tai-Guang Wu, Taipei (TW)

(73) Assignee: General Life Biotechnology Co., Ltd., Taipei (TW)

( * ) Notice: Subject to any disclaimer, the term of this patent is extended or adjusted under 35 U.S.C. 154(b) by 176 days.

(21) Appl. No.: 12/003,564

(22) Filed: Dec. 28, 2007

(65) Prior Publication Data

US 2009/0104641 A1    Apr. 23, 2009

(30) Foreign Application Priority Data

Oct. 19, 2007   (TW) ............................... 96139126 A

(51) Int. Cl.
   *G01N 33/72*   (2006.01)
(52) U.S. Cl. ...................................... 436/66
(58) Field of Classification Search ................ None
   See application file for complete search history.

(56) References Cited

U.S. PATENT DOCUMENTS

| 4,876,205 | A | * | 10/1989 | Green et al. | ................... | 436/66 |
| 5,089,420 | A | * | 2/1992 | Albarella et al. | .............. | 436/66 |
| 5,385,846 | A | * | 1/1995 | Kuhn et al. | ............... | 205/777.5 |
| 2004/0045821 | A1 | * | 3/2004 | Cui et al. | ............... | 204/403.02 |

OTHER PUBLICATIONS

Schmidt et al. Inclusion Complexation of Tetrathiafulvalene in Clyclodextrins and Bioelectroanalysis of the Glucose-Glucose Oxidase Reaction; Chemical Engineering Science, vol. 50, No. 12 (1995) pp. 1867-1876.*

* cited by examiner

*Primary Examiner*—Rebecca E. Prouty
*Assistant Examiner*—Paul C. Martin
(74) *Attorney, Agent, or Firm*—Birch, Stewart, Kolasch & Birch, LLP

(57) ABSTRACT

An electrochemical method and a test strip for detecting hemoglobin in a specimen are provided. The method includes the steps of providing the specimen with a reagent including a buffer solution, a surfactant and an electron mediator, tetrathiafulvalene, modified by cyclodextrin; detecting electric current produced by reaction of the hemoglobin and the electron mediator in the specimen under a potentiostatic condition; and calculating a concentration of the hemoglobin in the specimen according to the detected electric current.

9 Claims, 6 Drawing Sheets

1

ELECTROCHEMICAL METHOD FOR DETECTING HEMOGLOBIN

CROSS-REFERENCES TO RELATED APPLICATIONS

This application claims the benefit of priority based on Taiwanese Patent Application No. 096139126 filed in Taiwan on Oct. 19, 2007 under 35 U.S.C. §119, of which the contents are incorporated herein by reference in its entirety.

BACKGROUND OF THE INVENTION

1. Field of Invention

The present invention relates to an electrochemical method and a test strip for detecting a hemoglobin concentration, and more particularly to an electrochemical method and a test strip for detecting a hemoglobin concentration in a whole blood specimen.

2. Description of Related Art

In a blood test, except blood sugar and cholesterol, hemoglobin is also an important item. At present, methods for detecting the hemoglobin include a specific gravity method using copper sulfate for measuring the specific gravity of the whole blood; an oxidation-reduction reaction method using the "heme", which has peroxidase activity; an immunological method using an antibody of HbA1 for detecting the hemoglobin in stool; a gas measuring method detecting the binding of carbon monoxide with hemoglobin; and a cyanmethemoglobin method, in which potassium ferricyanide ($K_3Fe(CN)_6$) converts hemoglobin into methemoglobin and further into cyanmethemoglobin with sodium cyanide (NaCN) or potassium cyanide (KCN), and then the absorbance is measured at a particular wavelength etc. However, the above methods still have many disadvantages.

For example, when an optical device is used for detection, a large amount of specimen is needed and specimens need to be pre-treated before the detection in order to avoid an inaccurate result owing to the interfered absorbance. The above test methods are not only time-consuming, but also need a large amount of blood or non-blood specimen. Furthermore, the unstable property of cyanmethemoglobin usually affects the accuracy of detection, and potassium cyanide is quite toxic.

Therefore, electrochemical detection, particularly, electrochemical test strip has gradually become an important method in biochemical tests because it is simply produced, low cost, widely used and portable. U.S. Pat. No. 7,138,041 discloses that a sensory strip is used in electrochemical detection. However, this patent is silent on how to improve the dissolution property of the electron mediator for detecting the hemoglobin in a specimen.

As a result, it is still desired to have an electrochemical method and a test strip for rapidly and accurately detecting hemoglobin in a small amount of specimen.

SUMMARY OF THE INVENTION

It is an object of the present invention to provide an electrochemical method and a test strip for detecting the hemoglobin concentration in blood or an aqueous specimen solution.

It is another object of the present invention to provide an electrochemical method and a test strip for rapidly detecting the hemoglobin concentration in blood or an aqueous specimen solution.

It is another object of the present invention to provide a method and a test strip for detecting a hemoglobin concentration or hematocrit in a specimen according to the value of electric current in inverse proportion to the hemoglobin concentration.

It is a further object of the present invention to provide a method and a test strip for detecting the hemoglobin concentration or hematocrit in a specimen according to the hemoglobin concentration in inverse proportion to a value of SOC (state-of-charge), which is integrated by electric current with time.

To achieve the above-mentioned and other objects, the present invention provides an electrochemical method for detecting hemoglobin or hematocrit in a specimen. The method of the present invention includes the steps of providing the specimen with a reagent including a buffer solution, a surfactant and an electron mediator such as tetrathiafulvalene or dimethylferrocene modified by cyclodextrin; detecting the electric current produced from a reaction of hemoglobin and an electron mediator in the specimen under a potentiostatic condition; and calculating a concentration of the hemoglobin in the specimen according to the measured electric current.

In the method of the present invention, tetrathiafulvalene or dimethylferrocene modified by cyclodextrin is used as an electron mediator. Under a potentiostatic condition, the electron mediator interacts with hemoglobin in the specimen directly. The hemoglobin concentration in blood or an aqueous specimen solution can be detected, and furthermore the hematocrit in the blood specimen can be calculated according to the electric current value or a value of SOC integrated by the electric current with time and the hemoglobin concentration, wherein both the electric current value and the value of SOC are in inverse proportion to the hemoglobin concentration.

The present invention further provides a test strip for detecting hemoglobin. The test strip includes an insulating substrate having a first surface and a second surface opposing to the first substrate; an electrode assembly including a working electrode formed on the first surface of the insulating substrate and connected to a cathode joint and including a reference electrode connected to an anode joint; a spacer layer partially covering the first surface of the insulating substrate and exposing at least a part of the electrode assembly to form an electrode reaction area; and a reagent layer formed on the electrode reaction area and including a buffer solution, a surfactant and an electron mediator, wherein the electron mediator is tetrathiafulvalene or dimethylferrocene modified by cyclodextrin.

DETAILED DESCRIPTION OF THE PREFERRED EMBODIMENTS

Figure 1:
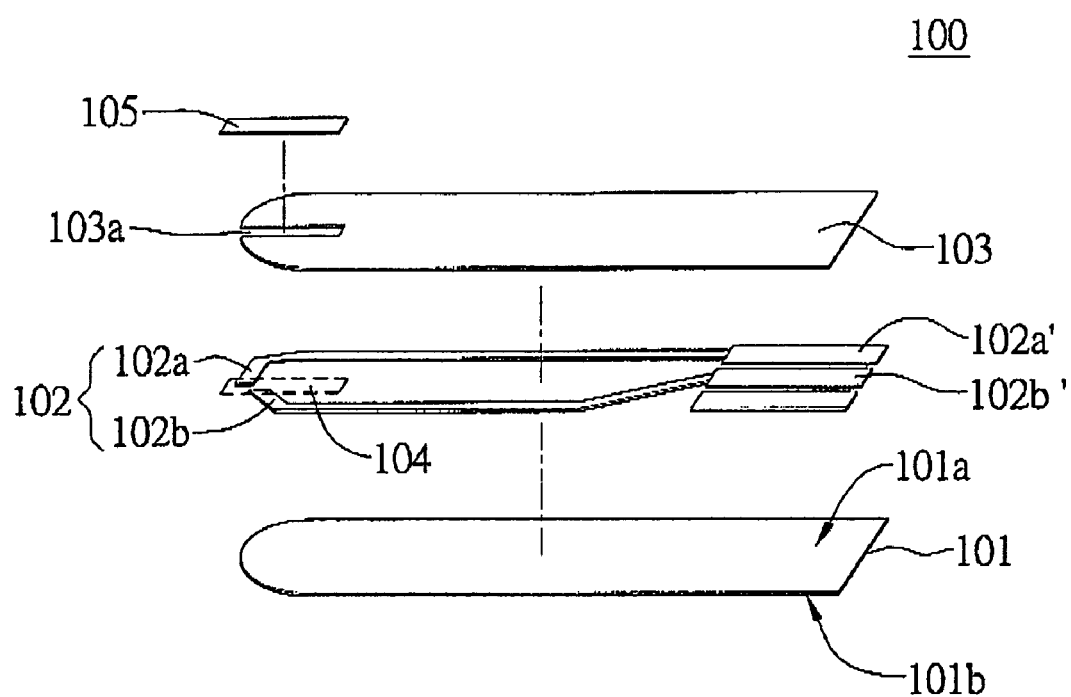
FIG. 1 is a schematic view showing the test strip according to the first embodiment of the present invention.

The electrochemical method for detecting hemoglobin in a specimen is provided in the present invention. In the method, the specimen is provided with a reagent including at least a buffer solution, a surfactant and an electron mediator. In the method of the present invention, the specimen can be a blood specimen, such as a whole blood specimen, plasma specimens or an aqueous specimen solution. In one embodiment, the whole blood specimen is detected. After the whole blood specimen is provided with the reagent, the surfactant interacts with red blood cells to release the hemoglobin from red blood cells. Subsequently, under a potentiostatic condition, the electron mediator is oxidized by the released hemoglobin.

In the reagent used in the method of the present invention, the buffer solution is used mainly for maintaining a specific range of pH, which is usually between 4 and 9 and preferably between 6 and 8. The buffer solution may be, but not limited to, a phosphate buffer solution, an acetate buffer solution and a citrate buffer solution etc. The concentration of the buffer solution is between 10 and 1000 mM, and preferably between 30 and 200 mM.

The surfactant in the reagent may be, but not limited to, Tween-20, Tween-80, Triton X-100, an acetylenic diol surface active agent such as SURFYNOL™ (Air Products and Chemicals, Inc., PA, U.S.A.) and Mega8, etc. The concentration of the surfactant ranges from 0.001% (w/v) to 10% (w/v), and preferably from about 0.1 to about 5% (w/v). The reagent used in the present invention can further contain a wetting agent such as cellulose, hydroxyethyl cellulose, polyethylene glycol, poly(vinyl alcohol), vinyl polymer, pyrrolidone or gelatin, etc.

In the method of the present invention, tetrathiafulvalene or dimethylferrocene modified by cyclodextrin is used as an electron mediator. The cyclodextrin may be, but not limited to, α-cyclodextrin, β-cyclodextrin, γ-cyclodextrin and water-solubly modified derivatives thereof unsubstituted or substituted by alkyl groups having 1 to 6 carbon atoms, hydroxyalkyl groups having 1 to 6 carbon atoms and/or maltosyl. Because the modified tetrathiafulvalene is well water-soluble at room temperature, an oxidation reaction of the modified tetrathiafulvalene and the hemoglobin in a specimen is performed under a potentiostatic condition. Thus, the hemoglobin concentration is detected according to the electric current, which is produced from the reaction.

In the embodiment, the electric current produced by the reaction is measured under the potentiostatic condition ranging from 0 to 1.5 volts, and preferably from 0.3 to 1.2 volts. Since the hemoglobin concentration is in inverse proportion to the value of the steady-state electric current produced by the hemoglobin and the modified tetrathiafulvalene or the value of SOC integrated by the electrical current with time, the hemoglobin concentration or the hematocrit in the specimen can be calculated according to the measured value of the steady-state electric current or the value of SOC integrated by the electrical current value with time.

FIG. 1 is a schematic view showing a test strip for detecting hemoglobin in a specimen according to the first embodiment of the present invention. In the embodiment, the test strip 100 includes an insulating substrate 101 having a first surface 101a and a second surface 101b opposing to the first surface 101a; an electrode assembly 102 including a working electrode 102a formed on the first surface 101a of the insulating substrate 101 and connected to a cathode joint 102a' and including a reference electrode 102b connected to an anode joint 102b'; a first spacer layer 103 partially covering the first surface 101a of the insulating substrate 101 and exposing a part of the electrode assembly 102 to form an electrode reaction area 104; and a reagent layer 105 formed on the electrode reaction area and including a buffer solution, a surfactant and an electron mediator such as tetrathiafulvalene or dimethylferrocene modified by cyclodextrin.

In the embodiment, the insulating substrate is used as a base of the test strip. The insulating substrate can be made of a soft material such as an insulating polymer material or a rigid material such as a ceramic material, glass or glass fiber etc. The insulating substrate may be, but not limited to, polycarbonate, polyester, polyether, polyamide, polyurethane, polyimide, polypropylene, polyethylene, polyvinyl chloride, glass, glass fiber, silicon dioxide or aluminum dioxide etc. The width of the base is between 3 and 15 millimeters, and preferably between 5 and 10 millimeters. The thickness of the base is between 50 and 800 micrometers, and preferably between 200 and 400 micrometers. The length of the base is between 1 and 8 centimeters, and preferably between 2 and 5 centimeters.

In the test strip 100 of the present invention, an electrically conductive material such as silver paste is printed on the first surface of the insulating substrate by screen printing so as to form a conductive wire area for connecting the electrode to the base. The carbon paste or silver/silver chloride is printed to form an electrode assembly comprising a working electrode and a reference electrode. Subsequently, a spacer layer 103 is attached on the first surface of the insulating substrate having the electrodes. The spacer layer 103 has an opening 103a exposing a part of the electrode assembly to form an electrode reaction area 104. The reagent layer 105 having a buffer solution, a surfactant and an electron mediator such as tetrathiafulvalen modified by cyclodextrin is disposed on the electrode reaction area 104 for releasing the hemoglobin from red blood cells in the specimen. Under the potentiostatic condition, the electron mediator in the reagent is oxidized by the released hemoglobin to produce electric current.

In the embodiment, the electric current produced by the reaction of the hemoglobin in the specimen and the electron mediator is measured under the potentiostatic condition ranging from 0 to 1.5 volts, and preferably from 0.3 to 1.2 volts. Since the hemoglobin concentration in the specimen is in inverse proportion to the value of the steady-state electric current produced by the hemoglobin and the modified tetrathiafulvalene (electron mediator) or the value of SOC integrated by the electrical current value with time, the hemoglobin concentration or the hematocrit in the specimen can be calculated according to the value of the steady-state electric current or the value of SOC.

Figure 2:
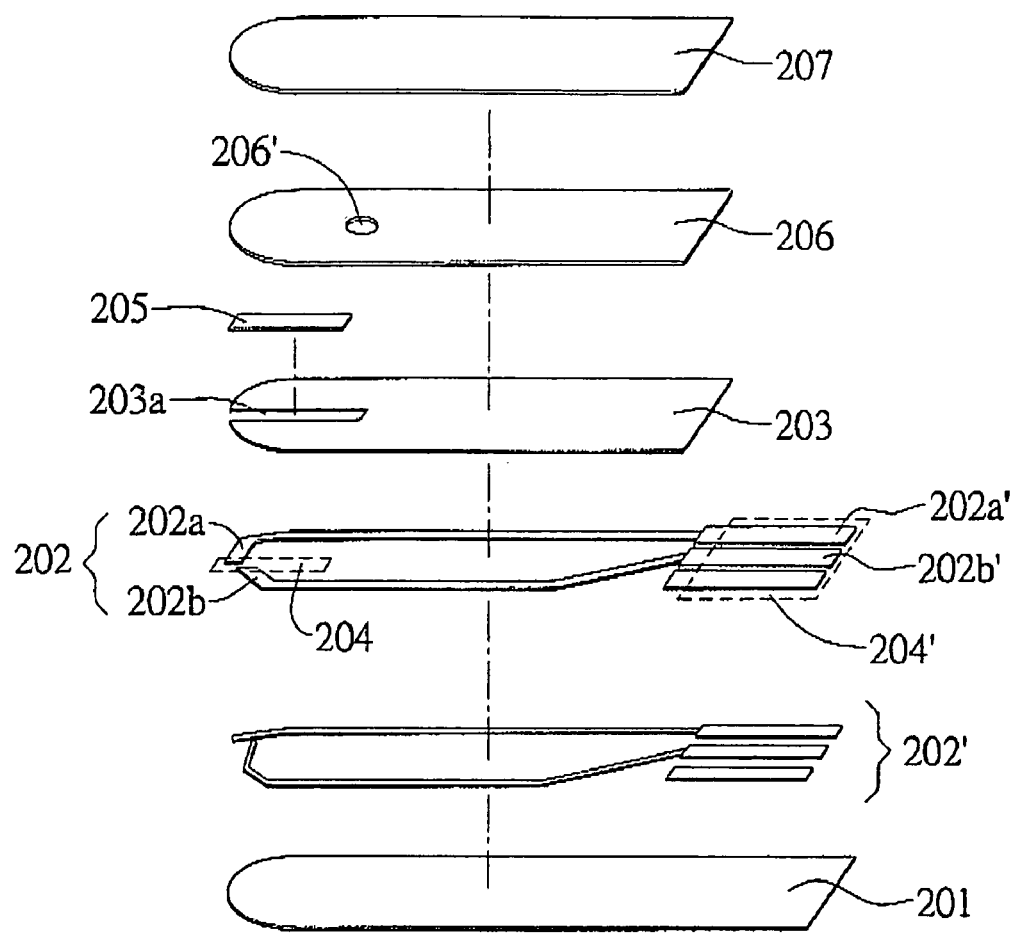
FIG. 2 is a schematic view showing the test strip according to the second embodiment of the present invention.

FIG. 2 is a schematic view showing a test strip for detecting the hemoglobin in a specimen according to the second embodiment of the present invention. In the embodiment, the test strip 200 includes an insulating substrate 201 having a first surface and a second surface opposing to the first surface; an electrode assembly 202 formed on the first surface of the insulating substrate 201, wherein an electrical conductive layer 202' is disposed between the insulating substrate 201 and the electrode assembly 202. The electrode assembly includes a working electrode 202a connected to a cathode joint 202a' and a reference electrode 202b connected to an anode joint 202b'; a first spacer layer 203 partially covering the first surface of the insulating substrate, exposing a part of electrode assembly 202 to form an electrode reaction area 204 and also exposing an electrical conductive area 204' formed by a cathode joint 202a' and an anode joint 202b'; a reagent layer 205 disposed on the electrode reaction area 204 and including a buffer solution, a surfactant and tetrathiafulvalene modified by cyclodextrin, which is used as an electron mediator; a second spacer layer disposed on the reagent layer; and a capping layer 207 used for capping the test strip 200.

In this embodiment, a specimen guiding groove 203a is formed on a section of the spacer layer corresponding to the reaction area 204, allowing the specimen to fill up the electrode reaction area 204 by capillary reaction and to interact with the electron mediator in the reagent layer 205. An opening 206' is formed on a section of the second spacer layer 206 corresponding to the reaction area 204, and a closed space having an internal volume of 0.5 to 5 microliters is formed by the section of the second spacer layer 206, the capping layer 207 and the electrode reaction area 204. Preferably, the closed space has an internal volume of 0.5 to 4 microliters, and more preferably has an internal volume of 1 to 2 microliters. The closed space is used for controlling the specimen volume, positioning the specimen filling and preventing the specimen from being contaminated.

Furthermore, the electrode distribution is designed according to the flowing direction of the specimen to make the working electrode contact the specimen first and the auxiliary electrode contact the specimen last when the specimen enters the reaction area. The resistance value is extremely high when the specimen has not filled up the two electrodes, and the resistance value is reduced sharply when the specimen fills up the two electrodes. Therefore, it can be confirmed whether the specimen fills up the closed space of the reaction area or not by monitoring the electric current, the electric potential or the value of SOC. After confirming that the specimen has completely filled up the closed space of the reaction area, the analysis is proceeded.

Figure 3:
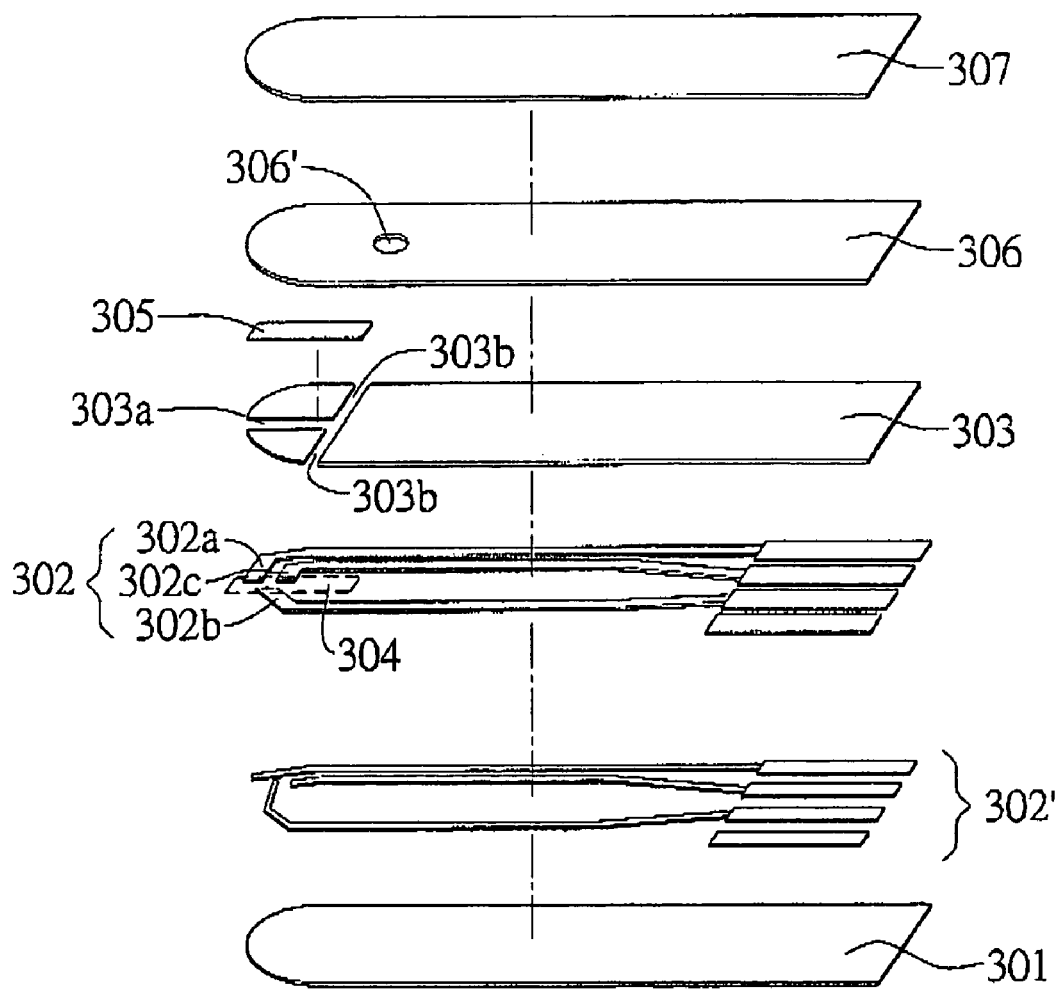
FIG. 3 is a schematic view showing the test strip according to the third embodiment of the present invention.

FIG. 3 is a schematic view showing a test strip for detecting the hemoglobin according to the third embodiment of the present invention. In this embodiment, the test strip 300 includes an insulating substrate 301 having a first surface and a second surface opposing to the first surface. An electrode assembly 302 is formed on the first surface of the insulating substrate through an electrically conductive layer 302' and includes a working electrode 302a, a reference electrode 302b and an auxiliary electrode 302c. A spacer layer 303 partially covers the first surface of the insulating substrate and exposes a part of the electrode assembly 302 to form an electrode reaction area 304. A reagent layer 305 is disposed on the electrode reaction area 304 and includes a buffer solution, a surfactant and tetrathiafulvalene modified by cyclodextrin, wherein the modified tetrathiafulvalene is used as an electron mediator. A second spacer layer 306 is disposed on the reagent layer 305. A capping layer 307 is disposed for capping the test strip 300.

In this embodiment, a specimen guiding groove 303a and an exhausting groove 303b are formed on a section of the spacer layer 303 corresponding to the reaction area 304, allowing the specimen to fill up the electrode reaction area 304 by capillary action. Thus, the specimen interacts with the electron mediator in the reagent layer 305. An opening 306' is formed on a section of a second spacer layer 306 corresponding to the reaction area 304, and a closed space is formed by the section of the second spacer layer 306, the capping layer 307 and the electrode reaction area 304. The closed space is used for controlling the specimen volume, positioning the specimen filling and preventing the specimen to be contaminated.

Figure 4:
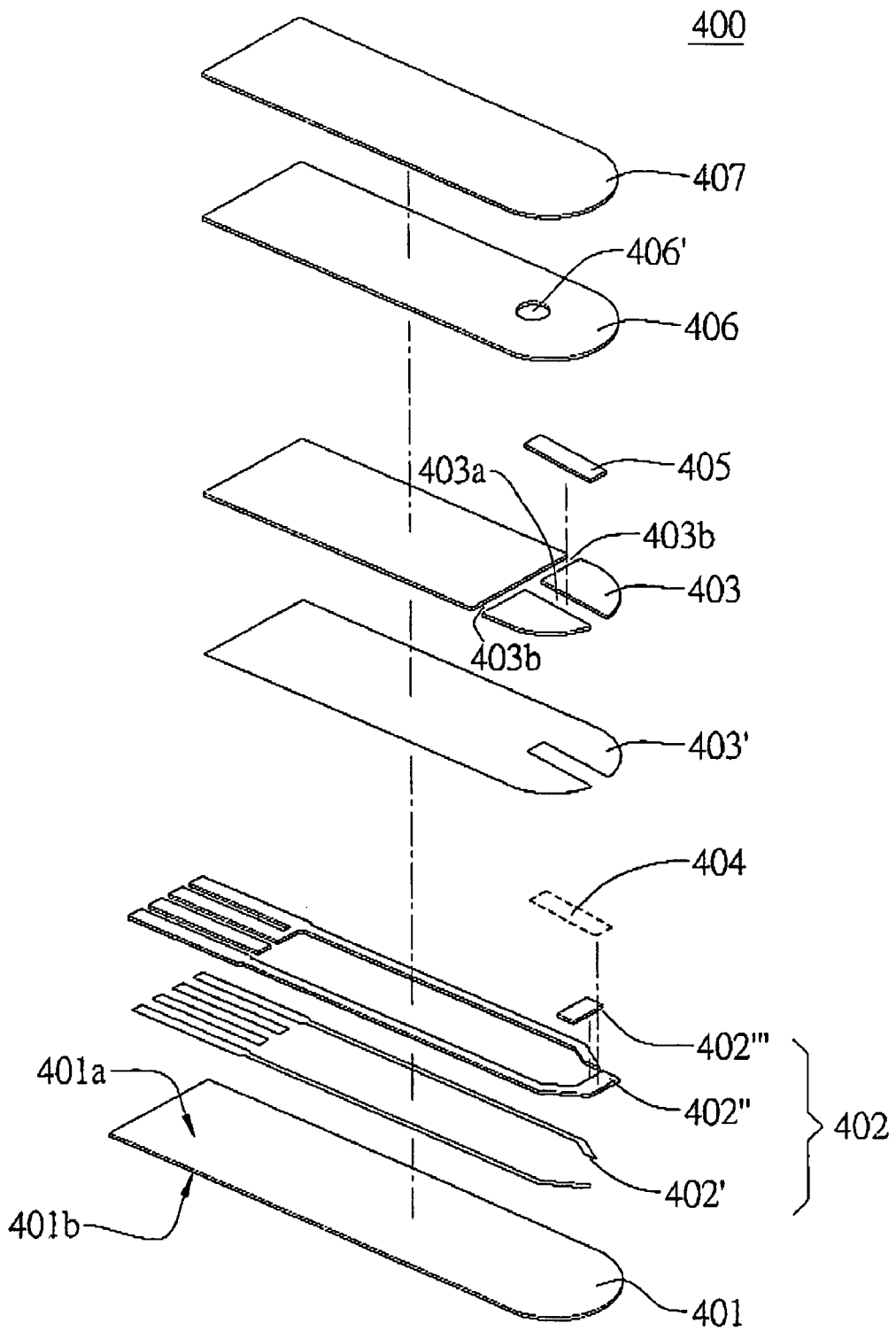
FIG. 4 is a schematic view showing the test strip according to the fourth embodiment of the present invention.

FIG. 4 is a schematic view showing a test strip for detecting the hemoglobin according to the fourth embodiment of the present invention. In this embodiment, the test strip 400 includes an insulating substrate 401 having a first surface 401a and a second surface 401b opposing to the first surface 401a; an electrode assembly 402 having a working electrode and a reference electrode both composed of an electrical conductive layer of silver paste 402', carbon paste 402" and silver/silver chloride paste 402''' in sequence formed on the first surface 401a of the insulating substrate 401; a spacer layer 403 partially covering the first surface of the insulating substrate via an insulating paste 403' and exposing a part of the electrode assembly 402 to form an electrode reaction area 404; a reagent layer 405 disposed on the electrode reaction area 404, wherein the reagent layer 405 has a buffer solution, a surfactant and tetrathiafulvaene modified by cyclodextrin, and the modified tetrathiafulvalene is used as an electron mediator; a second spacer layer 406 disposed on the reagent layer 405; and a capping layer 407 formed for capping the test strip 400.

In this embodiment, a specimen guiding groove 403a and an exhausting groove 403b are formed on a section of the spacer layer 403 corresponding to the reaction area 404, allowing the specimen to fill up the electrode reaction area 404 by capillary action. Thus, the specimen interacts with the electron mediator in the reagent layer 405. An opening 406' is formed on a section of a second spacer layer 406 corresponding to the reaction area 404, and a closed space is formed by the section of the second spacer layer 406, the capping layer 407 and the electrode reaction area 404. The closed space is used for controlling the specimen volume, positioning the specimen filling and preventing the specimen to be contaminated.

The specimen volume used in the test strip of the present invention is only about 0.5 microliter. It takes 5 to 10 seconds to perform the detection in the present invention. Hence, the hemoglobin can be detected or the hematocrit can be calculated rapidly and accurately in the present invention.

The embodiments below further illustrate the features and effects of the present invention, but not limit the scope of the present invention.

EXAMPLE

Preparative Example 1

A mixture of tetrathiafulvalene (TTF) (0.102 g, 0.5 μmole), hydroxypropyl methyl-β-cyclodextrin (2.555 g, 1.75 μmole) and deionized water (10 milliliter) was added into a dark container for avoiding light and stirred overnight at room temperature. Subsequently, the mixture was centrifuged at 6000 rpm for 10 minutes, the supernatant was retained, and then an electron mediator solution comprising TTF (50 mM) and hydroxypropyl methyl-β-cyclodextrin (175 mM) was obtained.

Preparative Example 2

Polyterephthalate base was used as a substrate. Electrical conductive silver paste was printed on the surface of the substrate by screen printing and dried at 60° C. for 5 minutes to form an electrical conductive silver paste layer. Subsequently, carbon paste was printed on the substrate by screen printing and dried at 60° C. for 5 minutes to form a working electrode, and then silver/silver chloride paste was also printed on the substrate by screen printing and dried at 60° C. for 5 minutes to form a reference electrode. After that, an insulating paste was printed on the substrate, dried at 105° C. for 5 minutes and attached by a first spacer sheet having a specimen guiding groove and an exhausting groove. A reaction reagent (5 microliters) having the electron mediator solution (10 mM, Preparative Example 1), polyvinyl pyrrolidone (2%), a potassium phosphate buffer solution (pH 8.0, 50 mM), potassium chloride (10-100 mM), Triton X-100 (1%) and carboxymethylcellulose (0.5%) was applied in a specimen guiding groove. After drying at 50° C. for 15 minutes, a second spacer sheet was attached to the substrate and a transparent sheet was pressed and fixed on the substrate to form a test strip 1.

Preparative Example 3

In this Example, the steps in Preparative Example 2 were repeated except the concentration of the electron mediator solution in the reaction reagent was 5 mM of TTF, to form a test strip 2.

Preparative Example 4

In this Example, the steps in Preparative Example 2 were repeated except the electron mediator solution in the reaction reagent was 5 mM of a tetrathiafulvalene (non-modified) solution, to form a test strip 3.

Test Example 1

Fresh vein blood was sampled, centrifuged and prepared to be the specimens with different hemoglobin concentrations from 0 to 26.6 g/dL. When testing, 2 microliters of the specimen was injected into the test strip 1, and the reaction in the test strip 1 was detected by an electrochemical analyzer (CH Instrument Co., Model 620A) under the condition of an electrical potential of 900 millivolts for 5 seconds. Results were analyzed by an automated analyzer (SYSMEX K-800™ (Sysmex American Inc., IL, U.S.A.)) and shown in Table 1.

TABLE 1

| Hemoglobin Concentration (g/dL) | Electric Current* (μA) |
|---|---|
| 0 | 50.4 |
| 3.3 | 45.4 |
| 6.6 | 41.9 |
| 10.0 | 37.1 |
| 13.3 | 32.7 |
| 16.6 | 26.5 |
| 20.0 | 17.7 |
| 23.3 | 14.7 |
| 26.6 | 11.8 |

*n = 18

Test Example 2

Fresh vein blood was sampled, centrifuged and prepared to be the specimens with different hemoglobin concentrations from 0 to 26.6 g/dL. When testing, 2 microliters of the specimen was injected into the test strip 2 or the test strip 3 (comparative example), and the reaction performed in the test strip was detected by an electrochemical analyzer (CH Instrument Co., Model 620A) under the condition of an electrical potential of 900 millivolts for 5 seconds. Results were analyzed by an automated analyzer (Sysmex K-800) and shown in FIG. 5.

Figure 5:
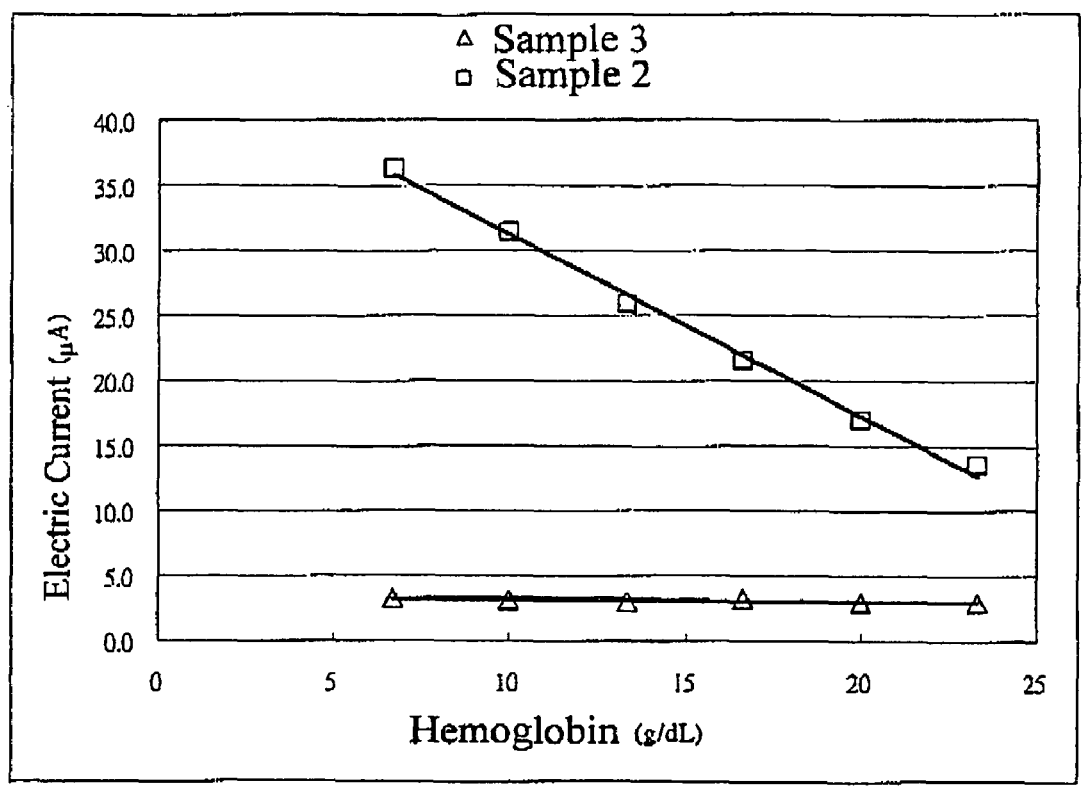
FIG. 5 is a diagram showing the results of the test example 2.

According to the results shown in FIG. 5, the test strip 3 having non-modified tetrathiafulvalene as an electron mediator cannot be used for recognizing the hemoglobin concentrations between 6.6 to 27 g/dL. However, in the test strip 2 having the tetrathiafulvalene modified by hydroxypropyl methyl-β-cyclodextrin as an electron mediator, the signal of electric current produced from the reaction is strong, i.e. the test strip 2 has an excellent performance in obtaining precise hemoglobin concentrations. The results of this Example show that tetrathiafulvalene modified by cyclodextrin as an electron mediator has the unexpected advantage during hemoglobin detection.

Test Example 3

Figure 6:
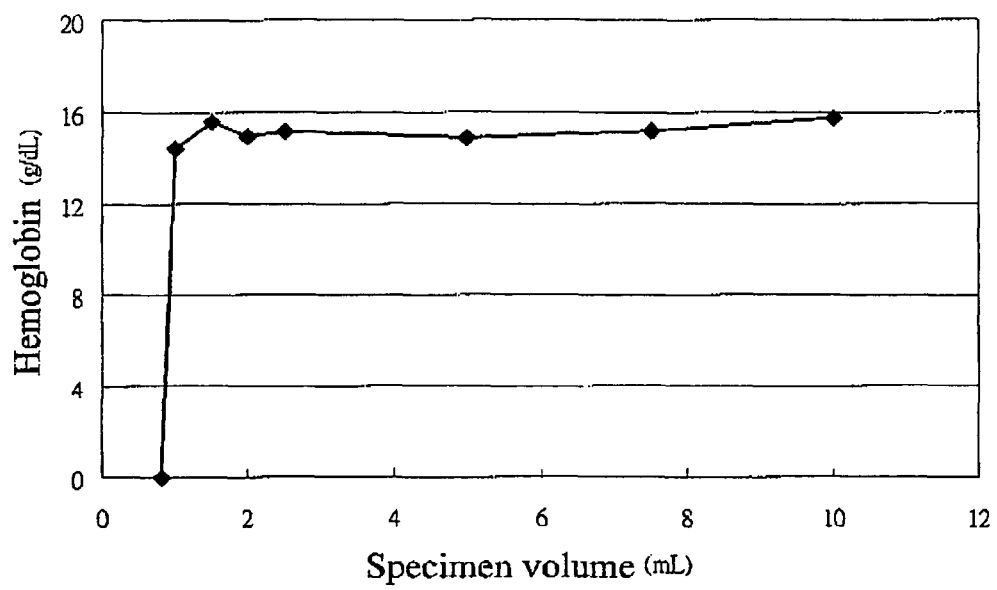
FIG. 6 is a diagram showing results of the test example 3.

In light of the steps performed in Test Example 1, different volumes of vein blood were absorbed into the test strips by capillary action for hemoglobin detection in this Example. As shown in FIG. 6, the test strip of the present invention does have an effect on controlling the specimen volume. Even though a large amount of specimen (2 microliters) is provided into the test strip, a hemoglobin concentration in the specimen can still be detected accurately.

What is claimed is:

1. An electrochemical method for detecting hemoglobin in a specimen, comprising the steps of:
   providing the specimen with a reagent comprising a buffer solution, a surfactant and an electron mediator of tetrathiafulvalene modified by cyclodextrin or dimethylferrocene modified by cyclodextrin;
   detecting electric current produced by a reaction of the hemoglobin and the electron mediator in the specimen under a potentiostatic condition; and
   calculating a concentration of the hemoglobin in the specimen according to the detected electric current.

2. The method of claim 1, wherein the buffer solution is one selected from the group consisting of a phosphate buffer solution, an acetate buffer solution and a citrate buffer solution.

3. The method of claim 1, wherein the buffer solution is used for maintaining a pH within a range of 4 to 9.

4. The method of claim 1, wherein the surfactant is a non-ionic surfactant.

5. The method of claim 1, wherein the cyclodextrin is one selected from the group consisting of α-cyclodextrin, β-cyclodextrin, γ-cyclodextrin and modified derivatives thereof unsubstituted or substituted by alkyl groups having 1 to 6 carbon atoms, hydroxyalkyl groups having 1 to 6 carbon atoms and/or maltosyl.

6. The method of claim 1, wherein the reagent further comprises a wetting agent.

7. The method of claim 6, wherein the wetting agent is one selected from the group consisting of cellulose, hydroxyethyl cellulose, polyethylene glycol, poly(vinyl alcohol), vinyl polymer, pyrrolidone and gelatin.

8. The method of claim 1, wherein the reaction is performed under a potentiostatic condition of 0 to 1.5 volts.

9. The method of claim 1, wherein the specimen is a whole blood specimen.

* * * * *